(12) United States Patent
Koschek

(10) Patent No.: US 10,709,330 B2
(45) Date of Patent: Jul. 14, 2020

(54) AMBULATORY MEDICAL TELEMETRY DEVICE HAVING AN AUDIO INDICATOR

(75) Inventor: Andrew G. Koschek, Ashland, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2159 days.

(21) Appl. No.: 11/719,302

(22) PCT Filed: Nov. 4, 2005

(86) PCT No.: PCT/IB2005/053620
§ 371 (c)(1),
(2), (4) Date: Sep. 3, 2010

(87) PCT Pub. No.: WO2006/051466
PCT Pub. Date: May 18, 2006

(65) Prior Publication Data
US 2011/0015493 A1    Jan. 20, 2011

Related U.S. Application Data

(60) Provisional application No. 60/628,092, filed on Nov. 15, 2004.

(51) Int. Cl.
*A61B 5/00* (2006.01)
*G06F 19/00* (2018.01)
(Continued)

(52) U.S. Cl.
CPC .............. *A61B 5/0002* (2013.01); *A61B 5/02* (2013.01); *A61B 5/6801* (2013.01); *G06F 19/34* (2013.01);
(Continued)

(58) Field of Classification Search
CPC ..... A61B 5/02; A61B 5/02438; A61B 5/0205; A61B 5/68; A61B 5/6887; A61B 5/404;
(Continued)

(56) References Cited

U.S. PATENT DOCUMENTS 3,346,857 A * 10/1967 Cromer, Jr. ............. G01F 23/60
340/328
4,237,448 A * 12/1980 Weinberg ..................... 340/7.62
(Continued)

FOREIGN PATENT DOCUMENTS

EP      0742553       11/1996
EP      0880936 A2    12/1998
(Continued)

*Primary Examiner* — Lori A. Clow
*Assistant Examiner* — Marie Archer

(57) ABSTRACT

An ambulatory medical telemetry device (10) is provided. This device includes at least one sensor (18) for detecting at least one physiological parameter of a patient and a housing that is securable to the patient. A circuit (50) is located in the housing for receiving and processing a signal representative of the physiological parameter from the sensor to generate recordable physiological data. An audible indicator (16) is located in the housing and operationally coupled to the circuit for generating an audio signal indicating at least one operational state of the device.

20 Claims, 2 Drawing Sheets

(51) Int. Cl.

| | | |
|---|---|---|
| *G08B 21/02* | (2006.01) | |
| *G08B 21/18* | (2006.01) | |
| *A61B 5/02* | (2006.01) | |
| *G16H 40/63* | (2018.01) | |
| *G16H 40/40* | (2018.01) | |
| *G08B 21/00* | (2006.01) | |

(52) U.S. Cl.
CPC ......... *G06F 19/3418* (2013.01); *G08B 21/02* (2013.01); *G08B 21/0211* (2013.01); *G08B 21/185* (2013.01); *G08B 21/187* (2013.01); *G16H 40/40* (2018.01); *G16H 40/63* (2018.01); *A61B 5/7405* (2013.01); *A61B 2505/07* (2013.01)

(58) Field of Classification Search
CPC ........ A61B 5/0002; G06F 19/34–3493; G08B 21/02–0211
USPC ................ 600/300–301, 363–365, 372–374, 600/377–379, 382–384, 386–394, 481, 600/485, 500–503, 508, 515–519, 600/529–531, 544–547, 549, 587–595; 128/920–925; 702/188–189, 2–3
See application file for complete search history.

(56) References Cited

U.S. PATENT DOCUMENTS

| | | | |
|---|---|---|---|
| 5,027,824 A | | 7/1991 | Dougherty et al. |
| 5,078,134 A | * | 1/1992 | Heilman et al. ................ 607/4 |
| 5,204,657 A | | 4/1993 | Prosser et al. |
| 5,335,664 A | | 8/1994 | Nagashima |
| 5,465,082 A | | 11/1995 | Chaco |
| 5,568,126 A | | 10/1996 | Andersen et al. |
| 5,579,001 A | | 11/1996 | Dempsey et al. |
| 5,873,369 A | | 2/1999 | Laniado et al. |
| 5,879,374 A | * | 3/1999 | Powers et al. ................... 607/5 |
| 6,278,890 B1 | | 8/2001 | Chassaing et al. |
| 6,304,780 B1 | * | 10/2001 | Owen et al. ..................... 607/5 |
| 6,693,585 B1 | * | 2/2004 | MacLeod ................. 342/357.55 |
| 7,707,458 B2 | * | 4/2010 | Miller et al. ..................... 714/25 |
| 2001/0027384 A1 | * | 10/2001 | Schulze et al. .............. 702/188 |
| 2002/0058906 A1 | * | 5/2002 | Lebel et al. .................... 604/65 |
| 2002/0087355 A1 | | 7/2002 | Rowlandson |
| 2003/0004547 A1 | * | 1/2003 | Owen et al. ..................... 607/5 |
| 2003/0065253 A1 | | 4/2003 | Stivoric et al. |
| 2003/0126593 A1 | | 7/2003 | Mault |
| 2003/0130590 A1 | | 7/2003 | Bui et al. |
| 2003/0212311 A1 | * | 11/2003 | Nova et al. ................... 600/300 |
| 2004/0193026 A1 | | 9/2004 | Scharf |
| 2005/0001728 A1 | * | 1/2005 | Appelt et al. ............... 340/573.1 |
| 2005/0179536 A1 | * | 8/2005 | Lederer, IV ................. 340/506 |
| 2005/0277429 A1 | * | 12/2005 | Laroia et al. ................. 455/458 |
| 2006/0217775 A1 | * | 9/2006 | Mills et al. ..................... 607/27 |
| 2007/0030164 A1 | * | 2/2007 | Lim ........................ 340/825.49 |
| 2009/0062682 A1 | * | 3/2009 | Bland et al. .................. 600/545 |
| 2010/0312085 A1 | * | 12/2010 | Andrews et al. ............. 600/365 |

FOREIGN PATENT DOCUMENTS

| | | |
|---|---|---|
| EP | 1017052 | 7/2000 |
| GB | 2312309 A | 10/1997 |
| GB | 2348726 A | 10/2000 |
| JP | 3040374 | 8/1997 |
| WO | 0209581 A1 | 2/2002 |
| WO | 02067122 A1 | 8/2002 |
| WO | 02089663 | 11/2002 |
| WO | 03082093 | 10/2003 |

\* cited by examiner

AMBULATORY MEDICAL TELEMETRY DEVICE HAVING AN AUDIO INDICATOR

CROSS REFERENCE TO RELATED APPLICATIONS

This application claims the benefit of U.S. provisional application Ser. No. 60/628,092 filed Nov. 15, 2004, which is incorporated herein by reference.

The present invention relates generally to ambulatory medical telemetry devices, and more particularly to an ambulatory medical telemetry device that includes an audible indicator for providing audio feedback to individuals in the physical vicinity of the device.

Monitoring of human physiological status data has received a high and growing level of interest in a number of medical, industrial, scientific and recreational disciplines. For example, monitoring of electrocardiography (ECG) data is a useful tool in diagnosing the condition of a patient's heart. Conventional medical telemetry devices allow instantaneous values of the physiological parameters to be viewed.

An ambulatory medical telemetry device is a portable electronic device that is secured to a patient for extended periods of time so that the physiological parameter(s) detected by the device can be continuously monitored and analyzed. The monitoring system may or may not include a recording unit for storing the data for subsequent analysis.

Patients may wear an ambulatory medical telemetry device in a variety of different settings, including their residence, a hospital or other medical care or rehabilitation institution. Regardless of the setting, clinical users need to ensure that the system is functioning properly. Since the clinical user is generally not as highly trained as a technician in the operation of the system, the user should ideally receive some assurance that the system has been correctly activated and is operating properly. In addition, when a patient is ambulatory, it can often be difficult to locate the patient. This can be critically important if a life-threatening or other emergency situation has arisen.

Accordingly, it would be desirable to provide means for feedback to the patient or other nearby individuals concerning the operation and status of the medical telemetry device and overall monitoring system.

In accordance with the present invention, an ambulatory medical telemetry device is provided. The device includes at least one sensor for detecting at least one physiological parameter of a patient and a housing that is securable to the patient. A circuit is located in the housing for receiving and processing a signal representative of the physiological parameter from the sensor to generate recordable physiological data. An audio transducer is located in the housing and operationally coupled to the circuit for generating an audio signal indicating at least one operational state of the device.

In accordance with one aspect of the invention, the audio signal generated by the audio transducer further indicates physiological-related information.

In accordance with another aspect of the invention, a wireless receiver is operationally coupled to the circuit and the audio transducer and is located in the housing for receiving a wireless paging signal such that the audio transducer, in response to the wireless signal, generates an audio paging signal.

In accordance with another aspect of the invention, the operational state of the monitor that is indicated is successful completion of a self-test.

In accordance with another aspect of the invention, the operational state of the monitor that is indicated is a failure of a self-test.

In accordance with another aspect of the invention, the operational state of the monitor that is indicated is a successful completion of a test result to obtain the physiological data.

In accordance with another aspect of the invention, the audio transducer generates at least one tone.

In accordance with another aspect of the invention, the audio transducer generates at least one different tone for each operational state of the monitor that is to be indicated.

In accordance with another aspect of the invention, the audio transducer generates a plurality of tones each corresponding to a different operational state of the monitor.

In accordance with another aspect of the invention, each of the plurality of tones differ in at least one characteristic selected from the group consisting of frequency, duration, intervals between tones and intensity.

In accordance with another aspect of the invention, one of the tones represents positive feedback and another of other of the tones represents negative feedback.

In accordance with another aspect of the invention, a wireless transceiver is operationally coupled to the circuit and the audio transducer and is located in the housing for, in a receiving state of operation, receiving a wireless paging signal such that the audio transducer, in response to the wireless signal, generates an audio paging signal.

In accordance with another aspect of the invention, the physiological parameter detected by the sensor is selected from the group consisting of electrocardiogram/respiration (ECG/RESP), electrocardiogram (ECG), invasive pressures, temperature, non-invasive blood pressure (NIBP), $SpO_2$/Pleth level, carbon dioxide level ($CO_2$), and cardiac output.

In accordance with another aspect of the invention, a method is provided for providing audible feedback from an ambulatory medical telemetry device securable to a patient. The method begins by detecting at least one physiological parameter of the patient and receiving and processing a signal representative of the physiological parameter to generate recordable physiological data. An audio signal is generated indicating at least one operational state of the device.

The present inventor has recognized that the aforementioned problems can be alleviated by equipping the ambulatory medical telemetry device with a transducer or other mechanism for generating an audible signal. The audible signal can provide feedback ensuring the user that the device and/or overall monitoring system is operating correctly. For example, the feedback may indicate the status of the patient being monitored, the status of the device hardware, or the status of algorithms employed in monitoring the patient. For instance, the audible signal may indicate that a measurement has been completed, that monitoring is inoperable, a self-test failed, that the device is otherwise unable to make a measurement, or that the measured value is outside of a predetermined range. The audible signal can also serve as a paging signal by which a caregiver can, for example, request that the patient return to their room or to aid in locating the patient after transmitting a wireless signal to the monitor.

The ambulatory device in which the present invention is employed can measure any of a variety of different physiological parameters, including, without limitation, electrocardiogram/respiration (ECG/RESP), electrocardiogram (ECG), invasive pressures, temperature, non-invasive blood pressure (NIBP), SpO$_2$/Pleth level, carbon dioxide level (CO$_2$), and cardiac output.

Figure 1:
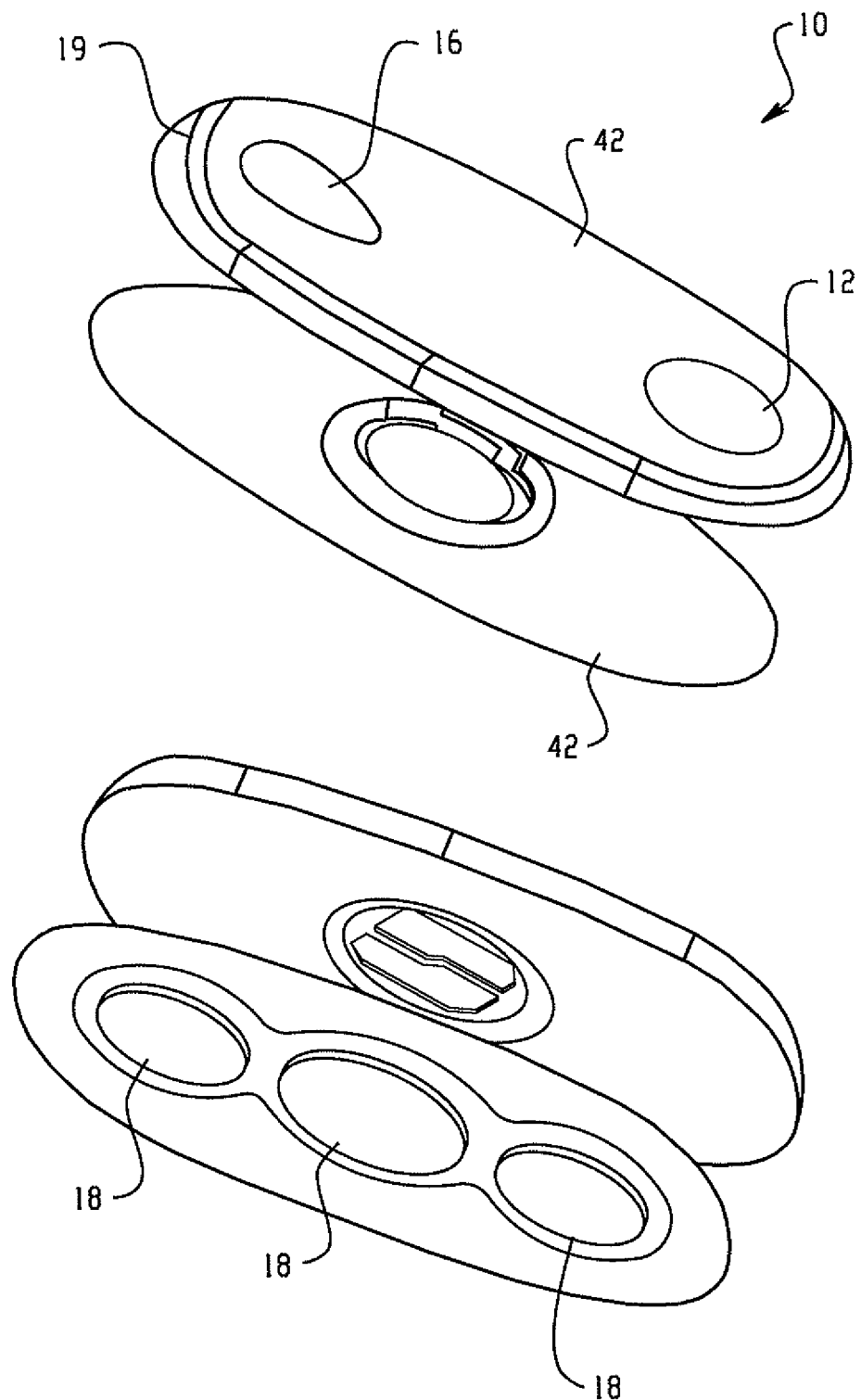
FIG. 1 shows a perspective view of an ambulatory medical telemetry device in accordance with the present invention.

A perspective view of an ambulatory medical telemetry device 10 in accordance with the present invention is shown in FIG. 1. The elements of the ambulatory device 10 are enclosed within a housing 42. A user interface 12, an audible indicator 16, a patient connector/sensor 18 and antenna(s) 19 are incorporated in the ambulatory device 10. The user interface 12, which may comprise a display, buttons and/or other actuators, and the like, may be used to activate the device, and select from among the different operational states that are available. The patient connector provides a connection between the circuitry or mechanisms of the ambulatory device 10 and sensors or other transducers affixed to the patient for monitoring the patient's condition. The antenna(s) 19 is used for wireless communication as described below. The ambulatory device 10 is carried by an ambulatory patient during the patient's normal activities, and the patient's physiological parameters of interest may be analyzed, monitored, displayed and recorded while the patient is ambulatory.

It should be noted that while ambulatory device 10 is typically designed to be simple and compact, in some embodiments of the invention it may include additional features such as other wireless link(s) for additional data exchanges or external battery packs to provide additional power for extended use. However, such features are optional and should not be construed as a limitation on the invention.

Figure 2:
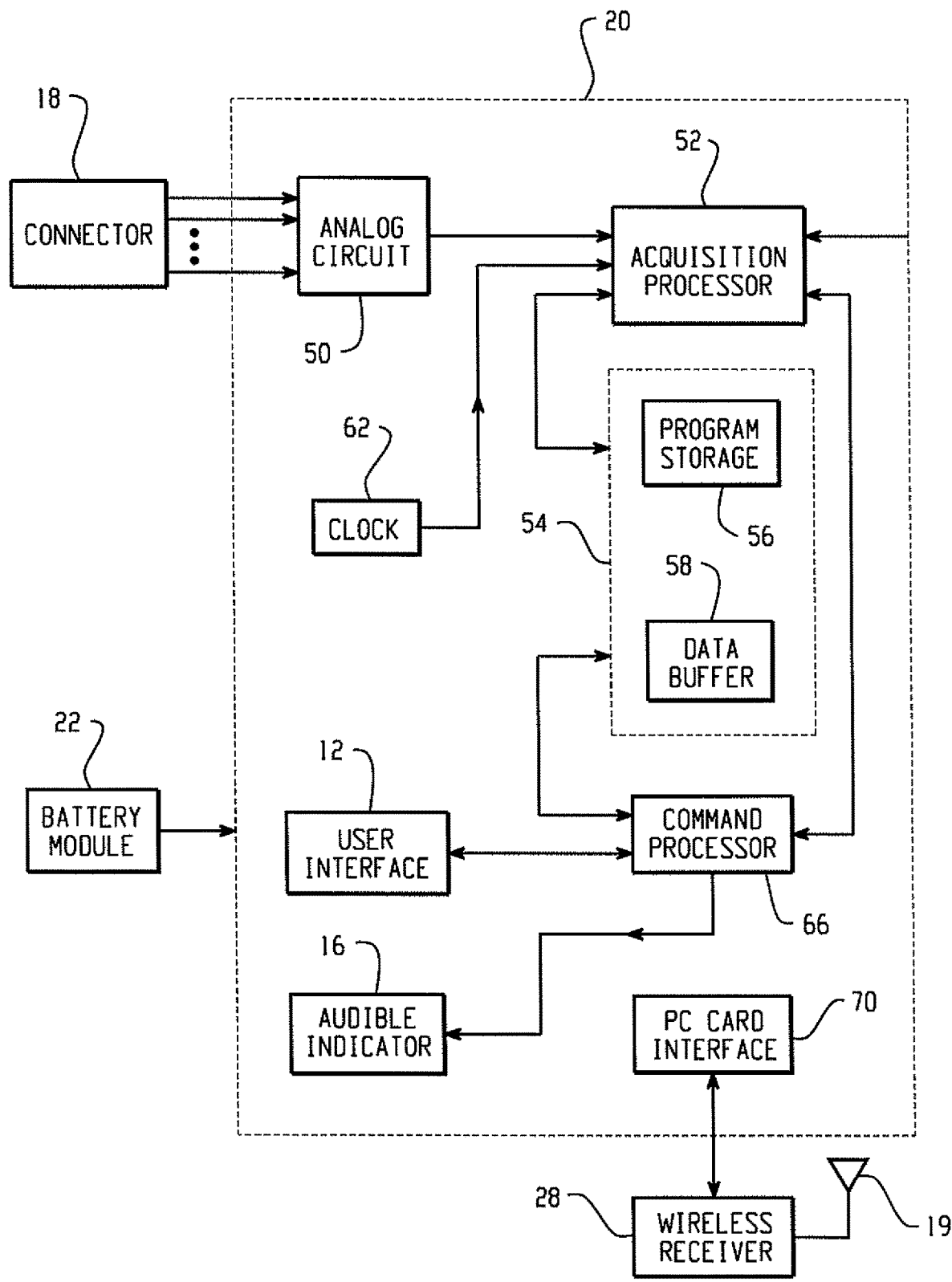
FIG. 2 shows a functional block diagram of one embodiment of the ambulatory medical telemetry device shown in FIG. 1.

A block diagram of one embodiment of the ambulatory medical telemetry device 10 is shown in FIG. 2. The contacts in patient connector/sensor 18 are connected to a circuit 50 in electronics module 20. As indicated above, sensors attached to the patient are connected through connector 18 to the ambulatory device 10. The circuit 50 processes physiological signals from the patient sensors. The outputs of circuit 50 are connected to an acquisition processor 52, which controls a portion of the device operation and converts physiological signals into useful data formats. The acquisition processor 52 is connected to a memory 54 which includes a program storage area 56 and a data buffer 58. The program storage area 56 is used to store a program for controlling operation of the acquisition processor 52. Data buffer 58 provides temporary storage of physiological data. A clock 62 is connected to acquisition processor 52. Portions of the ambulatory device 10 may be powered down when not in use to save battery power.

A command processor 66 is connected to acquisition processor 52 and to memory 54. The program storage area 56 is used to store programs for controlling operation of the command processor 66. The command processor 66 also controls transmission and reception of information through wireless alert transceiver 28 as described below. In one embodiment of the invention the wireless transceiver 28 is an integrated radio frequency telemetry unit. In some embodiments of the invention the full functionality of a transceiver may not be required, in which case only a wireless receiver or a wireless transmitter may be employed, depending on the requirements of the particular monitor. An audible indicator 16 is connected to the command processor 66. Audible indicator 16 may be a simple audio transducer that generates one or more tones. Alternatively, audible indicator 16 may be a more complex component that generates a variety of different tones or tunes, or voice. The audible indicator 16 may be able to vary the duration and intensity of the tone or tones.

The audible indicator 16, under control of the command processor 66, generates an audio signal that represents various operational states or conditions, thereby providing, audio feedback to the patient or other individual in the vicinity of the patient. The feedback that is provided may be negative feedback (if, for example, the monitor is inoperable or fails a self-test, or if the monitor is otherwise unable to make a measurement, or if the measured value is outside of a predetermined range). On the other hand, the feedback that is provided may be positive feedback, indicating, for example, that a self-test has been successfully completed, that a measurement has been successfully obtained, or the like. The audible indicator 16 may distinguish between positive and negative feedback in a variety of different ways. For example, if a tone is employed, the duration, intensity, and/or the frequency of the tone may be different for each type of feedback. Alternatively, a different tune may be employed for the different types of feedback.

The audible signal can also be used for a variety of other purposes. For instance, the audible signal can serve as a paging signal by which a caregiver can locate the patient after transmitting a wireless signal to the monitor. More specifically, in some embodiments of the invention the audible indicator 16 may be used to provide a paging feature. In this embodiment, wireless transceiver 28 (or wireless receiver) receives a wireless command signal from a central station (e.g., a nurse's station) or other location that activates the audible indicator 16. In this way the sound emanating facilitates the location of the device and/or the patient.

In some cases the paging feature can be used in two different ways. In particular, it can be used to request or page the patient to return to some predetermined location, e.g., his or her room. When used in this manner the audible signal has a distinctive tone or tune recognizable by the patient as a paging signal requesting the patient to return to the predetermined location. For example, such a paging signal could be a periodic tone having a fixed volume. On the other hand, the paging feature can also be used to find the ambulatory device, whether or not it is secured to the patient. In this case the paging signal advantageously may be different from the paging signal used to instruct the patient to return to the predetermined location. For example, the tone or tune may be continuous and at its maximum possible volume so that the device can be readily located.

In those embodiments of the invention providing the functionality of wireless transmission, wireless transceiver 28 can transmit the physiological data to a remote location for analysis. Also, in the event of an emergency as indicated by the physiological parameter being measured, the transceiver 28 can send an alert to a remote location to notify the emergency responder. In some embodiments of the invention the wireless transmitter 28 may send the data to a device that in turn forwards the data to the responder over a telephony or computer network. For example, if the monitor is to be used primarily in the patient's residence, the wireless transmitter 28 may forward the data to a specially enabled telephone that is also located in the residence.

In operation, the acquisition processor 52 acquires signals representing the physiological parameter being measured from circuit 50, converts the signals to data and may store the data in data buffer 58. In some cases the acquisition processor 52 can also check alarm limits (e.g., a life-threatening event) with respect to the physiological data. For example, if physiological data is being measured, the acquisition processor 52 may check the data for the occurrence of abnormal heartbeats. The alarm limits may be stored in program storage area 56 or any other appropriate location that can be accessed by acquisition processor 52. If the acquisition processor 52 determines that an alarm limit has been exceeded, indicative of an emergency situation, the acquisition processor 52 can activate audible indicator 16 via command processor 66.

Although various embodiments are specifically illustrated and described herein, it will be appreciated that modifications and variations of the present invention are covered by the above teachings and are within the purview of the appended claims without departing from the spirit and intended scope of the invention. For example, while the various components have been depicted as discrete elements, those of ordinary skill in the art will recognize that the functionality of those elements may be embodied in hardware, software, or any combination thereof, and thus are not necessarily embodied in discrete physical components.

The invention claimed is:

1. An ambulatory medical telemetry device, comprising:
at least one sensor configured for detecting at least one physiological parameter of a patient;
a housing securable to the patient;
a circuit located in said housing and configured for receiving and processing a signal representative of the physiological parameter from the at least one sensor to generate recordable physiological data;
at least one processor located in said housing and connected to the circuit, said at least one processor programmed to perform a self-test of an overall operation and each of a plurality of operational states of the ambulatory medical telemetry device, the plurality of operational states including at least three operational states; and
an audible indicator located in said housing and operationally coupled to said circuit and said at least one processor to generate an audio signal indicating at least one operational state of the device including a successful completion of the self-test indicating the operational state is operating correctly for each of the plurality of operational states of the ambulatory medical telemetry device;
wherein said audible indicator is configured to generate a plurality of different tones for indicating each of the overall operation and each operational state of the ambulatory medical telemetry device, each different tone corresponding to a different operational state of the device, the plurality of different tones further including a tone indicating the successful completion of the self-test for each of the plurality of operational states of the ambulatory medial telemetry device.

2. The device of claim 1, wherein said audio signal generated by the audible indicator further indicates physiological-related information.

3. The device of claim 1, further comprising:
a wireless receiver operationally coupled to the circuit and the audible indicator and located in said housing for receiving a wireless paging signal such that the audible indicator, in response to the wireless paging signal, generates an audio paging signal.

4. The device of claim 3, wherein said audible indicator generates a plurality of different tones indicative of each different operational state and the audio paging signal.

5. The device of claim 1, wherein one of the operational states of the device indicates a successful completion of a test result to obtain the physiological data.

6. The device of claim 1, wherein each of said plurality of tones differs in at least one characteristic selected from the group consisting of frequency, duration, intervals between tones, intensity, and tunes.

7. The device of claim 1, wherein at least one of the tones represents positive feedback, and at least one of the tones represents negative feedback in response to the self-test for the overall operation and each operational state of the device.

8. The device of claim 1, wherein the physiological parameter detected by the sensor includes at least one of:
electrocardiogram/respiration (ECG/RESP),
invasive pressures,
temperature,
non-invasive blood pressure (NIBP),
$SpO_2$/Pleth level,
carbon dioxide level ($CO_2$), and
cardiac output.

9. A method for providing audible feedback from an ambulatory medical telemetry device securable to a patient and communicating with a remote system, said method comprising the steps of:
performing a self-test for each of a plurality of operational states of the ambulatory medical telemetry device and an overall operation of the ambulatory medical telemetry device to monitor physiological data;
detecting a plurality of physiological parameters of the patient;
receiving and processing a signal representative of the physiological parameters to generate recordable physiological data; and
generating an audio signal indicating the overall operation and each of the plurality of operational states of the device which includes a successful result of the self-test indicating the operational state is operating correctly, the audio signal including a plurality of different tones for the overall operation and each of a plurality of operational states of the ambulatory medical telemetry device, each different tone corresponding to a different operational state of the device;
wherein the self-test includes testing the operational states of:
a status of the patient;
a status of algorithms employed by the device;
an inability to make a measurement;
a measurement outside a range; and
receipt of a paging signal.

10. The method of claim 9, wherein said audio signal further indicates physiological-related information.

11. The method of claim 10, further comprising the steps of:
converting multiple physiological signals processed by a circuit into a format for transmission;
transmitting the multiple physiological signals to the remote system to generate a wireless paging signal;
receiving the wireless paging signal; and
in response to the wireless signal, generating an audio paging signal.

12. The method of claim 11, wherein one of the operational states of the device indicates a failure of the self-test.

13. The method of claim 11, wherein said audio signal comprises each of a plurality of tones each corresponding to a different one of:
a status of the patient;

a status of algorithms employed by the device;
an inability to make a measurement;
a measurement outside a range; and
receipt of a paging signal.

14. The method of claim 9, wherein one of the operational states of the device indicates a successful completion of a test for obtaining the physiological data.

15. The method of claim 9, wherein each of said plurality of tones differs in at least one characteristic selected from the group consisting of frequency, duration, intervals between tones, and intensity.

16. The method of claim 9, wherein at least one of the tones represents positive feedback, and at least one of the tones represents negative feedback.

17. The method of claim 9, wherein the physiological parameter that is detected includes at least two of:
electrocardiogram/respiration (ECG/RESP),
invasive pressures,
temperature,
non-invasive blood pressure (NIBP),
$SpO_2$/Pleth level, carbon dioxide level ($CO_2$), and cardiac output.

18. The method of claim 9, further comprising the steps of:
receiving a first wireless paging signal and, in response, generating a first audio paging signal and receiving a second wireless paging signal and, in response, generating a second audio paging signal, respectively, wherein the first and second audio paging signals are audibly distinctive from one another.

19. The method of claim 18, wherein one of the first and second audio paging signals indicates a request to the patient to return to a predetermined location.

20. The method of claim 19, wherein the second audio paging signal is used to locate the ambulatory medical telemetry device.

* * * * *